United States Patent
Wu et al.

(10) Patent No.: US 6,297,061 B1
(45) Date of Patent: *Oct. 2, 2001

(54) SIMULTANEOUS PARTICLE SEPARATION AND CHEMICAL REACTION

(75) Inventors: Caicai Wu; Bernhard Weigl, both of Seattle; Margaret A. Kenny, Edmonds; Paul Yager, Seattle, all of WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/501,732

(22) Filed: Feb. 10, 2000

Related U.S. Application Data

(60) Continuation of application No. 09/335,930, filed on Jun. 18, 1999, which is a division of application No. 08/938,585, filed on Sep. 26, 1997, now abandoned.

(51) Int. Cl.⁷ .................................................. G01N 33/543
(52) U.S. Cl. ........................... 436/518; 436/52; 436/53; 436/172; 436/177; 436/178; 436/180; 422/81; 422/82; 422/82.05; 210/85; 210/94; 210/96.1; 210/511; 210/634; 210/739; 210/745; 210/746; 210/198.2; 210/243; 210/805
(58) Field of Search ............................... 436/52, 53, 172, 436/177, 178, 180, 518; 422/81, 82, 82.05; 210/85, 94, 96.1, 511, 634, 739, 745, 746, 198.2, 243, 805

(56) References Cited

U.S. PATENT DOCUMENTS

| | | |
|---|---|---|
| 4,214,981 | 7/1980 | Giddings .................... 209/155 |
| 4,250,026 | 2/1981 | Giddings .................... 209/155 |

(List continued on next page.)

FOREIGN PATENT DOCUMENTS

| | | | |
|---|---|---|---|
| WO 93/22053 | 11/1993 | (WO) | ................. B01L/3/00 |
| WO 96/04547 | 2/1996 | (WO) | ............. G01N/27/00 |
| WO 96/15576 | 5/1996 | (WO) | ............. H02K/44/02 |

OTHER PUBLICATIONS

Johnstone et al. (Eds). Immunochemistry 1; A Practical Approach, pp. 147–176, 193–214.*

(List continued on next page.)

*Primary Examiner*—Christopher L. Chin
*Assistant Examiner*—Minh-Quan Pham
(74) *Attorney, Agent, or Firm*—Greenlee, Winner and Sullivan, P.C.

(57) ABSTRACT

This invention provides a method and apparatus for detecting the presence of analyte particles in a sample fluid also comprising larger particles, particularly blood. It exploits diffusion to provide simultaneous filtering of the larger particles and reaction of the analyte particles. A sample stream and a reagent stream join on the upstream end of a laminar flow reaction channel and flow in adjacent laminar streams. The reagents can be in solution or immobilized on a bead. The analyte particles diffuse from the sample stream into the reagent stream, leaving behind the larger particles in the residual sample stream. In the reagent stream the analyte particles react with reagent particles and form product particles, thereby creating a product stream. At the downstream end of the reaction channel, the residual sample stream and the product stream are divided. The product particles are then detected, preferably optically, in the product stream. Prior to detection, the product stream can undergo further filtering or separation, or can join a second reagent stream to form secondary product particles. This apparatus and method can be used to implement competitive immunoassays or sandwich immunoassays using enzymatically or fluorescently labeled immunoreagents. The apparatus and method can also be used to synthesize products, in which case two reagent streams join in the laminar flow reaction channel.

51 Claims, 11 Drawing Sheets

U.S. PATENT DOCUMENTS

| | | | |
|---|---|---|---|
| 4,608,869 | 9/1986 | Lerner | 73/644 |
| 4,675,300 | 6/1987 | Zare et al. | 436/172 |
| 4,737,268 | 4/1988 | Giddings | 209/12 |
| 4,849,340 * | 7/1989 | Oberhardt | 435/13 |
| 4,894,146 * | 1/1990 | Giddings | 209/12 |
| 4,954,715 | 9/1990 | Zold | 250/461.1 |
| 4,962,037 | 10/1990 | Jett et al. | 435/6 |
| 5,039,426 | 8/1991 | Giddings | 209/12 |
| 5,121,988 | 6/1992 | Blesener et al. | 356/442 |
| 5,141,651 | 8/1992 | Giddings | 210/748 |
| 5,144,224 | 9/1992 | Larsen | 324/71.4 |
| 5,156,039 | 10/1992 | Giddings | 73/1 R |
| 5,193,688 | 3/1993 | Giddings | 209/155 |
| 5,278,048 | 1/1994 | Parce et al. | 436/29 |
| 5,281,531 | 1/1994 | Schramm | 436/518 |
| 5,288,463 | 2/1994 | Chemelli | 422/58 |
| 5,326,692 | 7/1994 | Brinkley | 435/6 |
| 5,366,608 | 11/1994 | Kambara | 204/299 R |
| 5,389,524 | 2/1995 | Larsen et al. | 435/29 |
| 5,427,946 | 6/1995 | Kricka et al. | 435/291 |
| 5,439,578 * | 8/1995 | Dovichi et al. | 204/299 |
| 5,444,527 | 8/1995 | Kosaka | 356/73 |
| 5,480,614 | 1/1996 | Kamahori | 422/70 |
| 5,552,885 * | 9/1996 | Steen | 356/246 |
| 5,560,889 | 10/1996 | Ogine | 422/82.05 |
| 5,585,069 | 12/1996 | Zanzucchi et al. | 422/100 |
| 5,599,432 | 2/1997 | Manz et al. | 204/451 |
| 5,602,039 | 2/1997 | van den Engh | 436/164 |
| 5,602,349 | 2/1997 | van den Engh | 73/864.85 |
| 5,635,358 | 6/1997 | Wilding et al. | 435/7.2 |
| 5,643,796 | 7/1997 | van den Engh | 436/50 |
| 5,674,743 | 10/1997 | Ulmer | 435/287.2 |
| 5,707,799 | 1/1998 | Hansmann et al. | 435/6 |
| 5,716,852 * | 2/1998 | Yager et al. | 436/172 |
| 5,726,404 | 3/1998 | Brody | 200/81 R |
| 5,726,751 | 3/1998 | Altendorf et al. | 356/246 |
| 5,747,349 | 5/1998 | van den Engh et al. | 436/172 |
| 5,748,827 | 5/1998 | Holl et al. | 385/134 |
| 5,750,063 | 5/1998 | Hoyt | 264/172.15 |
| 5,790,727 | 8/1998 | Dhadwal et al. | 385/38 |
| 5,932,100 * | 8/1999 | Yager et al. | 210/634 |
| 5,942,443 | 8/1999 | Parce et al. | 436/514 |
| 5,948,684 * | 9/1999 | Weigl et al. | 436/52 |
| 5,971,158 * | 10/1999 | Yager et al. | 209/155 |
| 5,972,710 * | 10/1999 | Weigl et al. | 436/34 |

OTHER PUBLICATIONS

Johnstone et al. (Eds). Immunochemistry 2; A Practical Approach, pp. 71–130, 197–256.*

Brody, J.P. and Yager, P., "Low Reynolds Number Micro–Fluidic Device," (Jun. 2–6, 1996) Solid–State Sensor and Actuator Workshop, Hilton Head, South Carolina, 105–108.

Verpoorte, E.M.J. et al., "Three–dimensional micro flow manifolds for miniaturized chemical analysis systems," (1994) *J. Micromech. Microeng.* 4:246–256.

Fuh. C.B. et al., "Rapid Diffusion Coefficient Measurements Using Analytical SPLITT Fractionation: Application to Proteins," (1993) *Anal. Biochem.* 208:80–87.

Giddings, J.C., "Continuous Separation in Split–Flow Thin (SPLITT) Cells: Potential Applications to Biological Materials," (1988) *Separation Science and Technology* 23(8 & 9):931–943.

Levin, S. and Tawil, G., "Analytical SPLITT Fractionation in the Diffusion Mode Operating as a Dialysis–like System Devoid of Membrane. Application to Drug–Carrying Liposomes," *Anal. Chem.* 65:2254–2261.

Williams, P.S. et al., "Continuous SPLITT Fractionation Based on a Diffusion Mechanism," (1992) *Ind. Eng. Chem. Res.* 31:2172–2181.

Maggio (1980), Enzymes as immunochemical label. In Enzyme–Immunoassay (Ed.Maggio). CRC Press. pp. 53–70.

* cited by examiner

SIMULTANEOUS PARTICLE SEPARATION AND CHEMICAL REACTION

CROSS-REFERENCE TO RELATED APPLICATIONS

This application is a continuation of co-pending application Ser. 09/335,930 filed Jun. 18, 1999, which is a divisional application of U.S. Ser. No. 08/938,585 filed Sep. 26, 1997, now abandoned.

FIELD OF THE INVENTION

This invention relates to simultaneous diffusion based filtering and chemical reaction of analytes in streams containing both these analytes and larger particles. The invention is useful, for example, for analyzing blood to detect the presence of small particles such as antigens in a stream containing cells, or for preparing small volumes of fluid products.

BACKGROUND OF THE INVENTION

It is possible to fabricate intricate fluid systems with channel sizes as small as a micron. These devices can be mass-produced inexpensively and are expected to soon be in widespread use for simple analytical tests. However, in chemical analysis of turbid fluids, notably blood, filtering of the larger particles such as cells is generally required prior to analysis, especially optical analysis. In clinical laboratories this is generally accomplished by centrifugation. The centrifugal force generated is a function of distance from the center, and thus centrifugation is not effective in a small scale apparatus. In chemical laboratories membrane filters are used to separate the larger particles. This can be used in microscale apparatus, but clogging of the filters with use makes them impractical.

The greater diffusion of small particles relative to larger particles can be used to partially separate the species. Diffusion is a process which can easily be neglected at large scales, but rapidly becomes important at the microscale. Due to extremely small inertial forces in such structures, practically all flow in microstructures is laminar. This allows the movement of different layers of fluid and particles next to each other in a channel without any mixing other than diffusion. Moreover, due to the small lateral distances in such channels, diffusion is a powerful tool to separate molecules and small particles according to their diffusion coefficients, which is usually a function of their size.

The present invention exploits diffusion to provide simultaneous filtering and chemical reaction, which facilitates the elimination of preprocessing of specimens containing particulate constituents, thus reducing the sample size and analytical time required.

SUMMARY OF THE INVENTION

This invention provides a method and apparatus for reacting small particles in a fluid also comprising larger particles. It provides simultaneous filtering of the larger particles and reaction of the small particles. The reactor can be followed by collection of or detection of the reaction products. The reactor exploits diffusion to separate the small primary particles from the larger particles. It utilizes microscale channels wherein diffusion becomes a significant factor and wherein the fluid flow is laminar. The reactor can be simply and inexpensively manufactured and can be disposed of after use. The reactor is capable of processing a fluid volume between about 0.01 microliters and about 20 microliters within a few seconds. Operation with sub-microliter volumes of sample fluid is a particular advantage for expensive reagents or for blood analysis. Larger volumes with correspondingly longer times can be used when preferred, for example viral detection in a sample with a low viral load.

The reactor can be used for analysis, in which case the inlet fluid, termed generically the primary fluid, is a sample fluid and the small particles, termed generically the small primary particles, are analyte particles. In this case the reactor is generally coupled with a detector. Alternatively, the reactor can be used to rapidly synthesize small volumes of product fluids. In this case the primary fluid is a reagent fluid and the small primary particles are reagent particles. This has particular application to making products starting from natural substances. In the following, the reactor is described for the analysis embodiment, but the description also applies to the synthesis embodiment.

The invention uses an "H" shaped reactor. In the H-reactor the crossbar of the H is a laminar flow reaction channel. On the upstream end of the crossbar a sample (primary) stream and a reagent stream enter through separate arms of the H, and the sample stream and the reagent stream flow in adjacent laminar streams in the crossbar. Because the flow is laminar, there is no turbulent mixing of the two streams, but the analyte particles diffuse from the sample stream into the reagent stream, leaving behind the larger particles in the residual sample stream. In the reagent stream the analyte particles react with reagent particles and form product particles, thereby creating a product stream. At the downstream end of the crossbar, the residual sample stream and the product stream divide into the two downstream arms of the H. The product particles can then be detected in the product stream.

Detection of the product particles can be performed using optical, electrical, chemical, electrochemical or calorimetric analysis, or any other technique in the analytical art. More than one detection technique can be used in the same system. The preferred embodiments use optical analysis or a combination of electrochemical and optical analysis. In optical detection, the product stream can be analyzed by luminescence, fluorescence or absorbance. To increase the signal in the detection zone the product stream channel can be broadened or convoluted. The product stream can connect to a flow cytometer for analysis, particularly a flow cytometer having a microfabricated flow channel.

An example of an application of this method is in competitive immunoassays in solution. The sample stream is whole blood containing native antigens. The reagent particles are antibodies bound to a fluorescently labeled antigen. In the reaction channel, the native antibodies diffuse into the reagent stream and displace the fluorescently labeled antigens. The product stream contains both native and fluorescently labeled antigens, some of which are free and some of which remain bound to antibodies. The relative amounts of free and bound fluorescently labeled antigen, which is a function of the amount of native antigen in the blood, can be measured.

Prior to detection, the product stream can undergo further filtering or separation. In particular the product stream can join with an extraction stream in a separation channel such that the product and extraction streams flow in adjacent laminar flow streams. Smaller particles in the product stream flow into the extraction stream for detection, preferably optical detection.

An example of utilizing the separating channel, is a competitive immunoassay as above wherein the antibody-fluorescently labeled antigen complex is immobilized on a microbead. In the separation channel, the free and bound fluorescently labeled antigen can be separated by diffusion. The free antigen that enters the extraction stream can be detected by fluorescence without interference from the antigen on the beads. In lieu of differential separation, the product stream can be coupled with a flow cytometer to measure the fluorescence intensity remaining on the beads. The bead can be magnetic, and a magnetic field can be used to pin the bead in the sample stream to allow reaction with the analyte particles. Following reaction, a reverse field returns the beads to the reagent stream.

The detection process can use a second reagent stream that joins with the product stream in a "T" configuration. The two streams flow in adjacent laminar streams, and small product particles from the product stream diffuse into the second reagent stream, or small reagent particles from the second reagent stream diffuse into the product stream. Depending on the diffusion process, in either or both streams the product particles react with the second reagent particles to form secondary product particles. The secondary product particles are detected as described above for primary product particles.

First and second reagent streams are usefull, for example, for sandwich immunoassays. The first reagent is a primary antibody which binds to an antigen from the sample to form a first product. The first regent is large enough to change the diffusion coefficient of the complex. The second reagent is a fluorescently labeled secondary antibody, which reacts with the first product to form a sandwich complex. The complex is detected as described above for primary products. The slower diffusion of the complexed relative to the uncomplexed labeled antibody is used to distinguish between the two, either by diffusional separation of the species or by the extent of depolarization of the fluorescence.

Second reagent streams are also utilized when the first reaction involves an enzymatically labeled rather than fluorescently labeled reagent. The difference in enzymatic activity of bound and unbound enzymatically labeled reagent particles allows measurement of the extent of reaction. Through the second reagent stream, a substrate which is sensitive to the enzyme joins the first reaction products. Reaction of the substrate and enzyme is then detected as described above for primary products.

The first or subsequent product streams can flow through a delay line to allow the reaction to be completed before detection or before joining a subsequent reagent stream. The first or subsequent product streams can also undergo filtering or diffusional separation before detection or before joining a subsequent reagent stream. The reagents can be immobilized on magnetic beads, and a magnetic field can be used to pin the beads for reaction or flushing steps in any of the reaction channels.

The sample stream may be any stream containing an analyte and also containing less diffusive particles, for example blood or other body fluids, contaminated drinking water, contaminated organic solvents, biotechnological process samples, e.g., fermentation broths, and the like. The analyte can be any smaller particle in the sample stream which is capable of diffusing into the reagent stream faster than the larger particles, so as to substantially leave the larger particles in the residual sample stream. Examples of analyte particles are hydrogen, calcium, sodium and other ions, dissolved oxygen, proteins such as albumin, organic molecules such as alcohols and sugars, drugs such as salicylic acid, halothane and narcotics, pesticides, heavy metals, organic and inorganic polymers, viruses, small cells and other particles. In the preferred embodiment wherein the sample stream is whole blood, small particles such as antigens diffuse rapidly across the channel, whereas larger particles such as blood cells diffuse slowly.

The larger particles in the sample stream may also be sensitive to the reagent. Because these do not diffuse into the reagent stream, they do not interfere with detection of the analyte. By diffusion of the analyte but not the larger particles, cross-sensitivities of reagents to larger sample components, a common problem, can be avoided. Furthermore, the reagent can be kept in a solution in which it displays its optimal characteristics. For example, cross-sensitivities to pH or ionic strength can be suppressed by using strongly buffered reagent solutions.

BRIEF DESCRIPTION OF THE DRAWINGS

FIG. 1, comprising

DETAILED DESCRIPTION OF THE INVENTION

This invention relates to the following co-pending Patent Applications, all of 5 which are incorporated by reference in their entirety: U.S. Ser. No. 08/625,808, "Microfabricated Diffusion-Based Chemical Sensor," filed Mar. 29, 1996, now U.S. Pat. No. 5,716,852; U.S. Ser. No. 08/829,679, "Microfabricated Diffusion-Based Chemical Sensor," filed Mar. 31, 1997, U.S. Pat. No. 5,972,710; U.S. patent application Ser. No. 08/900,926, "Simultaneous Analyte Determination and Reference Balancing in Reference T-Sensor Devices," filed Jul. 25, 1997, U.S. Pat. No. 5,948,684; U.S. Ser. No. 08/621,170 "Fluorescent Reporter Beads for Fluid Analysis," filed Mar. 20, 1996, U.S. Pat. No. 5,747,349; U.S. Ser. No. 08/663,916, "Microfabricated Differential Extraction Device and Method," filed Jun. 14, 1996, U.S. Pat. No. 5,932,100; U.S. Ser. No. 08/534,515, "Silicon Microchannel Optical Flow Cytometer," filed Sep. 27, 1995, U.S. Pat. No. 5,726,751; PCT No. 96/15566 "Silicon Microchannel Optical Flow Cytometer," filed Sept. 27, 1996, WO 97/12223; U.S. Ser. No. 08/823,747, "Device and Method For 3-Dimensional Alignment of Particles in Microfabricated Flow Channels," filed Mar. 26, 1997; U.S. Ser. No. 08/876,038, "Adsorption-Enhanced Differential Extraction Device," filed Jun. 13, 1997, U.S. Pat. No. 5,971,158; U.S. Ser. No. 60/049,533, "Method For Determining Concentration of a Laminar Sample Stream," filed Jun. 13, 1997, U.S. Pat. No. 5,974,867; U.S. Ser. No. 08/938,584, "Device for Rapidly Joining and Splitting Fluid Layers," filed concurrently herewith; Ser. No. 08/938,093, "Multiple Analyte Diffusion Based Chemical Sensor," U.S. Pat. No. 6,007,775.

The channel cells and method of this invention are designed to be carried out such that all flow is laminar. In general, this is achieved in a device comprising microchannels of a size such that the Reynolds number for flow within the channel is below about 1, preferably below about 0.1. Reynolds number is the ratio of inertia to viscosity. Low Reynolds number means that inertia is essentially negligible, turbulence is essentially negligible, and the flow of the two adjacent streams is laminar, i.e. the streams do not mix except for the diffusion of particles as described above. Flow can be laminar with Reynolds number greater than 1. However, such systems are prone to developing turbulence when the flow pattern is disturbed, e.g., when the flow speed of a stream is changed, or when the viscosity of a stream is changed. The preferred embodiments of this invention utilize liquid streams, although the methods and devices are also suitable for use with gaseous streams.

Figure 1A:
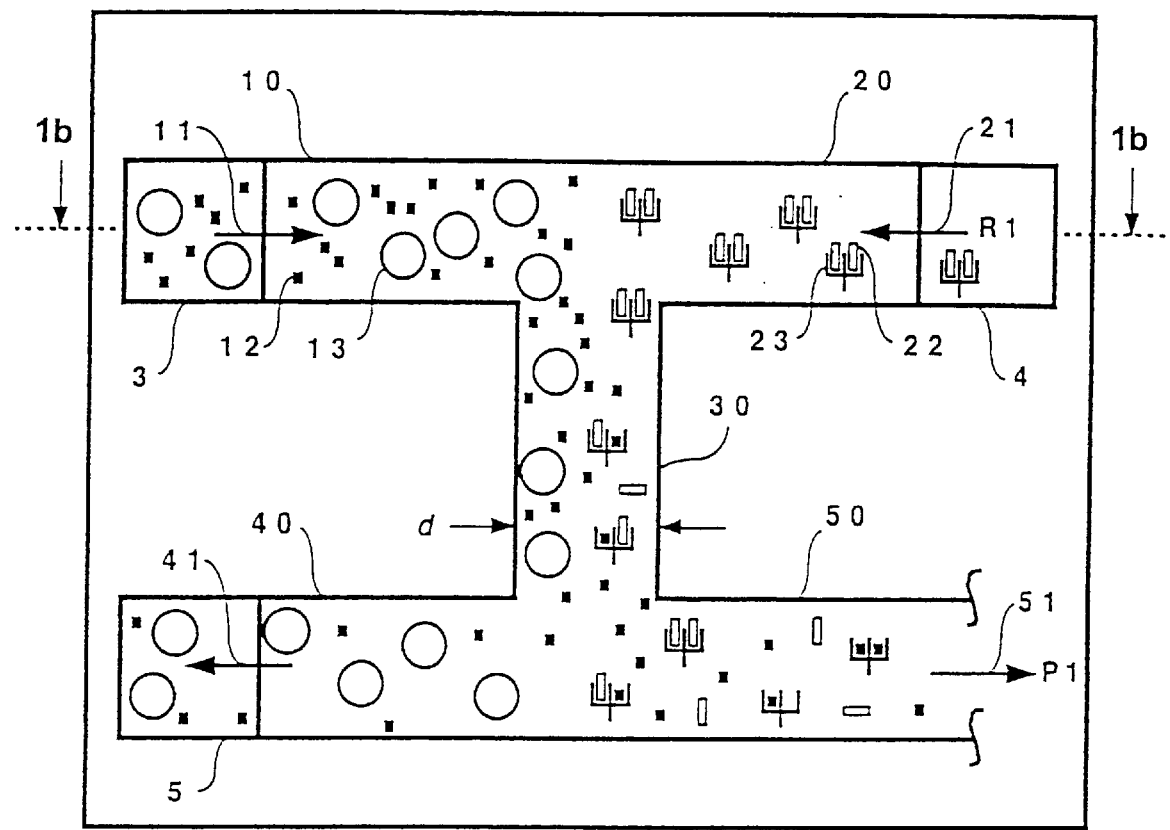
FIGS. 1a–b, is an H reactor illustrated with a competitive immunoassay. The reactor is shown in (a) plan view and (b) cross section.
Figure 1B:
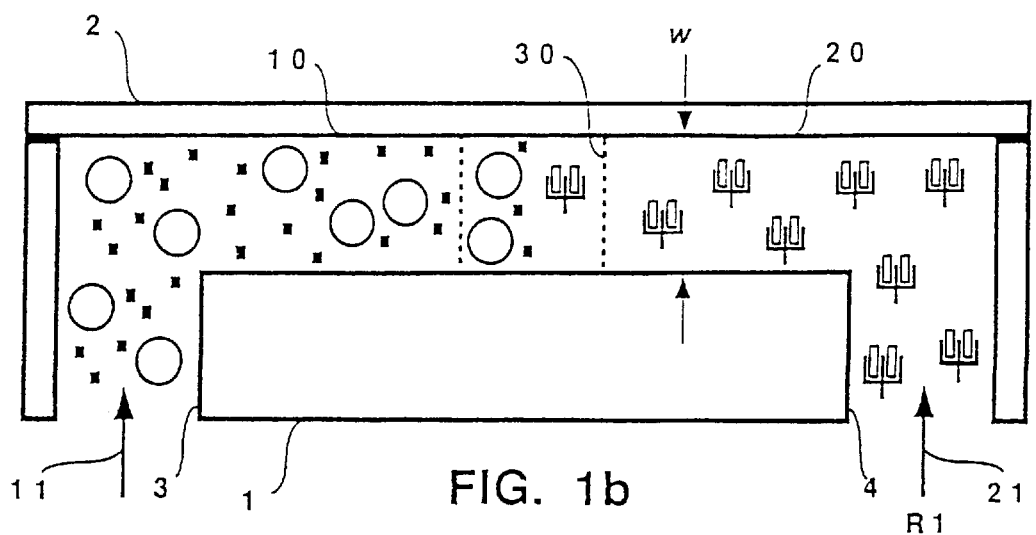

The H reactor of this invention is illustrated in plan view in FIG. 1a and in cross section in FIG. 1b. The channel cell containing the H reactor comprises substrate plate 1 and coverplate 2. Sample (primary) stream 11 enters sample stream inlet channel 10 through inlet 3. The sample contains analyte (small primary) particles 12 and larger particles 13. The term "particles" refers to any species, including dissolved and particulate species such as molecules, cells, suspended and dissolved particles, ions and atoms. In this example the sample is whole blood, the analyte is an antigen, and the larger particles are blood cells. Reagent stream 21, also labeled R1, separately enters reagent stream inlet channel 20 through inlet 4. The term "separately" is used for streams having individual rather than shared flow channels. In this example the reagent particles are antibody 23 bound with labeled antigen 22.

The sample and reagent streams join in reaction channel 30 where they flow in adjacent laminar streams, also called companion streams. The term "adjacent" is used herein for both side by side streams, as in FIG. 1, and layered streams, as in FIG. 13. The sample stream enters one side of the reaction channel and the reagent stream enters the other side. The term "side" as used herein refers to both left and right, as in channel 30 of FIG. 1, and top and bottom, as in channel 30 of FIG. 13.

Because the flow in the reaction channel is laminar, there is no turbulent mixing of the streams. However, by diffusional mixing the small analyte particles diffuse into the reagent stream and react with the reagent particles to form product particles. The diffusion direction is termed the depth, labeled d, and the orthogonal dimension is termed the width, labeled w. In this example, the native and labeled antigen compete for binding sites on the antibody. By the end of the reaction channel, the reagent stream has become a first product stream, P1, and the sample stream is a residual sample stream. The residual sample stream 41 exits through residual sample stream outlet channel 40 and outlet 5, and product stream 51 flows into product stream channel 50.

In the illustrated embodiment the reaction in channel 30 is a complex formation between antigen and antibody. The term "reaction" as used herein includes any interaction between the analyte particle and reagent particle which leads to a detectable change. It includes chemical reaction, physical binding, adsorption, absorption (for example when the analyte particle is sucked inside a porous reagent particle such as a zeolite), antibody reaction, nucleic acid binding, ion pairing, ion exchange, chromatographic type reaction and receptor hormone reaction.

The product stream flows into a product particle detection channel. The term product particles refers to all particles in the product stream. They can be, for example, new species formed from reaction, or reagent particles the concentration of which depends on the extent of reaction with analytes. In the example of FIG. 1, the displaced labeled antigen and the antibody with native antigen are both product particles. The detection channel of this invention may be coupled to external detecting means for detecting changes in the reagent particles carried within the product stream as a result of contact with analyte particles. Detection and analysis is done by any means known to the art, including optical means, such as absorption spectroscopy, luminescence or fluorescence, by chemical indicators which change color or other properties when exposed to the analyte, by immunological means, electrical means, e.g. electrodes inserted into the device, electrochemical means, radioactive means, or virtually any microanalytical technique known to the art including magnetic resonance techniques, or other means known to the art to detect the presence of an analyte such as an ion, molecule, polymer, virus, DNA sequence, antigen, microorganism or other factor. Field effects which are ion or chemical sensitive can be measured in the detection channel. Preferably optical means are used, and antibodies, DNA sequences and the like are attached to optical markers. Examples of detection channels are discussed below, following description of further embodiments of the H reactor.

Figure 2:
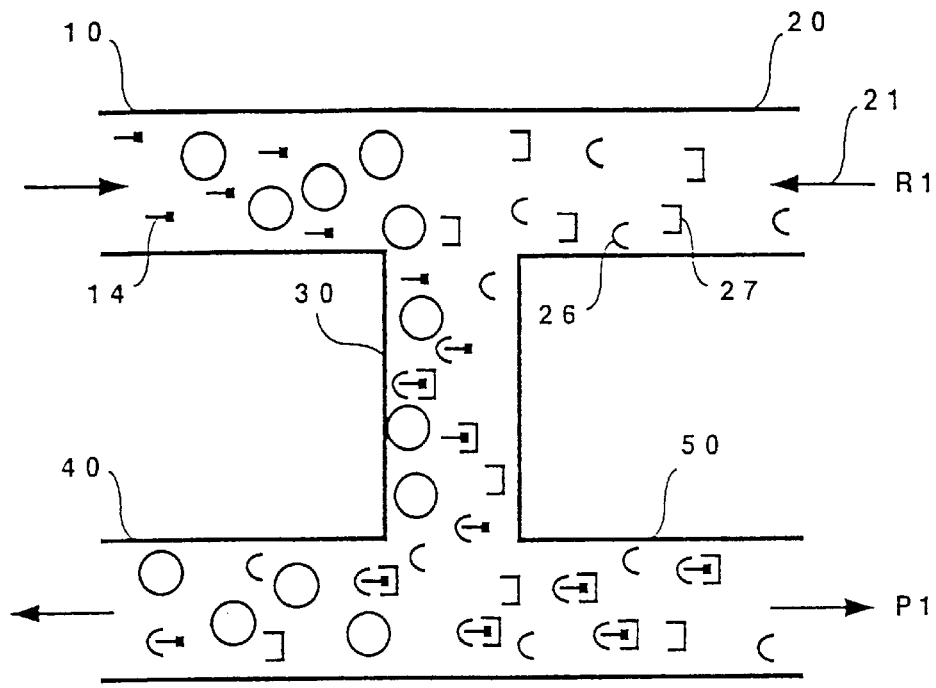
FIG. 2 is an H reactor illustrated with a sandwich immunoassay.

A different reaction scheme is illustrated in FIG. 2. Analyte 14 is an antigen. Reagent stream 21 contains two types of reagent particles, primary antibody 26 and labeled secondary antibody 27. Both antibodies react with the antigen to form product particles, which exit through product channel 50. The secondary antibody can be, for example, fluorescently, luminescently or enzymatically labeled. The first antibody can be sufficiently large that it reduces the diffusion coefficient of the complex enough to diffusionally distinguish between the complexed and uncomplexed labeled antibody.

Figure 3:
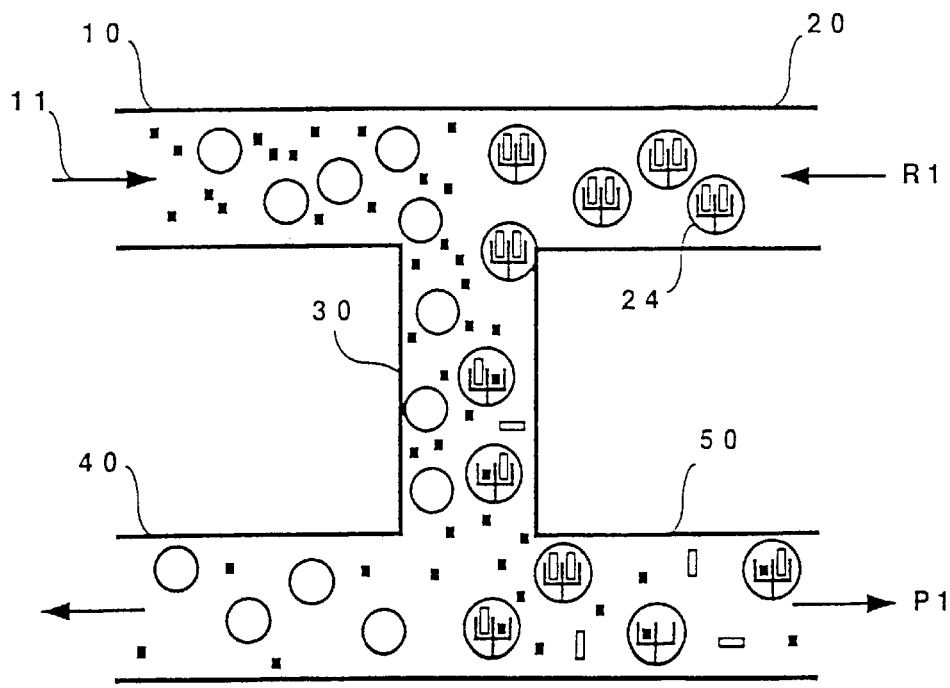
FIG. 3 is an H reactor illustrated with a competitive immunoassay wherein the antibody is immobilized on a bead.

The reagent particles can be reporter particles immobilized on beads to form reporter beads 24, as shown in FIG. 3. Each reporter bead comprises a bead having a plurality of at least one type of reporter molecules immobilized thereon. A property of the reporter bead, such as fluorescence, luminescence, absorbance or chemical activity, is sensitive to a corresponding analyte. The use of reporter beads allows for a plurality of analytes to be measured simultaneously through a single reagent inlet because the beads can be tagged with different reporter molecules. The reporter bead is illustrated herein with the competitive immunoassay. It could also be used with a sandwich immunoassay or with other reporter molecules.

Figure 4:
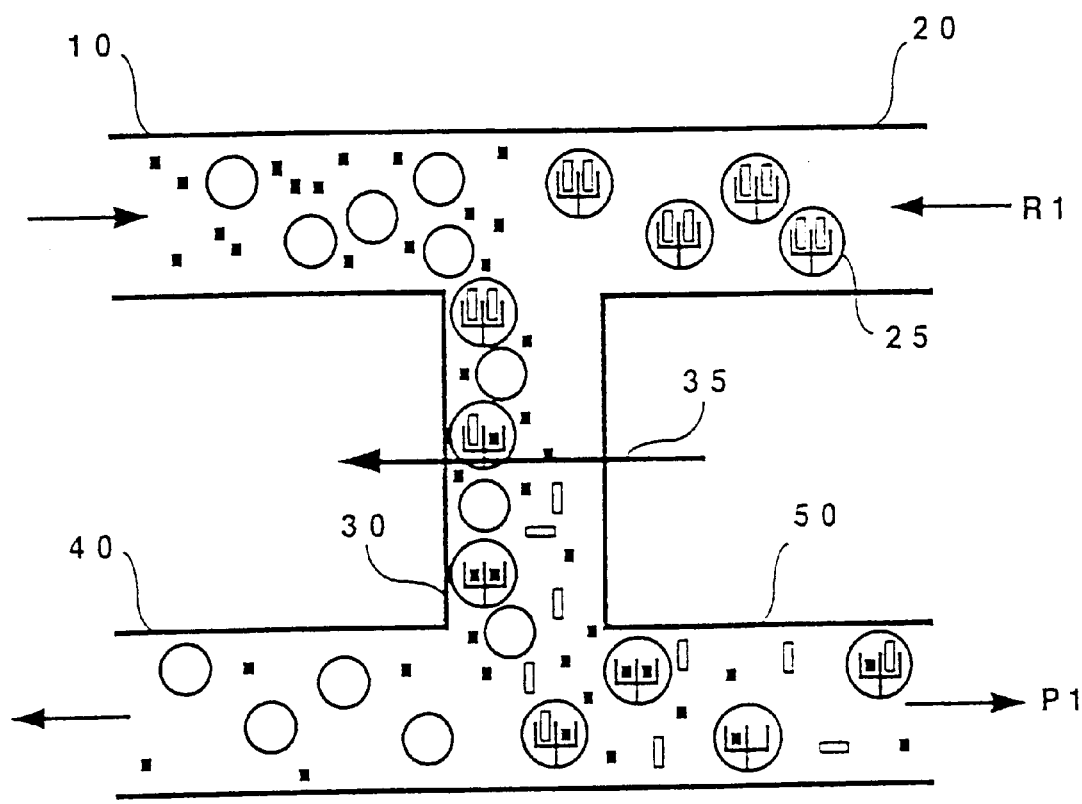
FIG. 4 is an H reactor illustrated with a competitive immunoassay wherein the antibody is immobilized on a magnetic bead and wherein a magnetic field is applied to pin the beads to one side of the reaction channel.

The reagent particles can be magnetic reporter beads 25, as shown in FIG. 4. Within reaction channel 30, transient magnetic field 35 pulls the beads into the sample stream for reaction with the analyte. The field is then reversed to pull the beads back to the product stream for analysis.

Following the H reactor, the product stream flows into a detection channel. Although many detection means can be used, optical detection is preferred. The detection channel can be probed with absorbance, luminescence or fluorescence measurement. The absorbance of the reagent particle can change upon reaction and the detection channel can be monitored in transmission. For this embodiment, the channel cell is made of an optically transparent material such as glass or plastic. The external optical apparatus can be very simple. The sensor can be illuminated on one side with a light source such as a light bulb and diffuser, and the absorbance can be detected on the other side with a camera. Alternatively the fluorescence of reagent particles can change in response to the analyte, in which case the fluorescence can be monitored. Alternatively, the reaction product can be luminescent. For reflection measurements the back side of the channel cell need not be transparent and is preferably made of a reflective material such as silicon.

Figure 5:
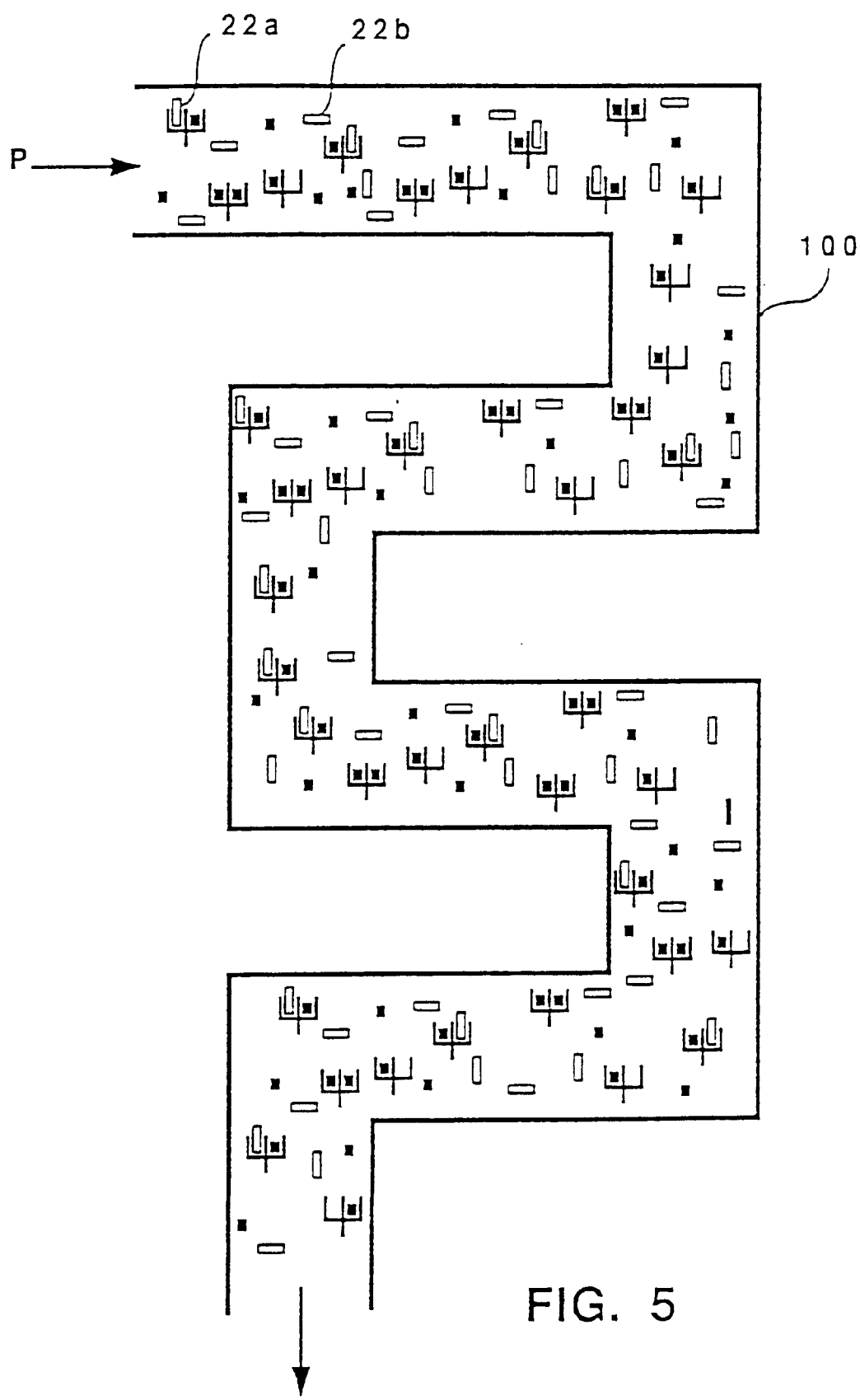
FIG. 5 is a convoluted detection channel for optical detection.
Figure 6:
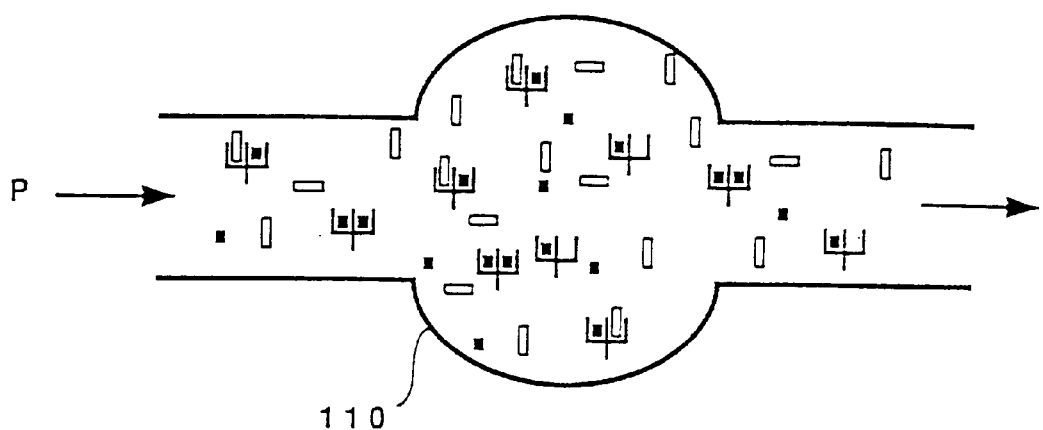
FIG. 6 is a broadened detection channel for optical detection.

For optical detection, the signal can be increased by using convoluted detection channel, as shown in FIG. 5. A product stream, P, enters the detection channel. There is a difference in optical properties between bound antigen 22a and unbound antigen 22b. It can be a difference in, for example, color, fluorescence intensity, or degree of polarization of the fluorescence. In this embodiment, detection channel 100 includes a series of turns, making a square wave geometry. The flow channel can be convoluted in any of a number of ways. In another embodiment, the flow channel is in the shape of a coil. In lieu of a convoluted channel, the channel can include a broadened region, as shown in detection channel 110 of FIG. 6. An external light source and photodetector are positioned about the detection channel for absorbance or fluorescence measurements. Only a photodetector is required for luminescence.

Figure 7:
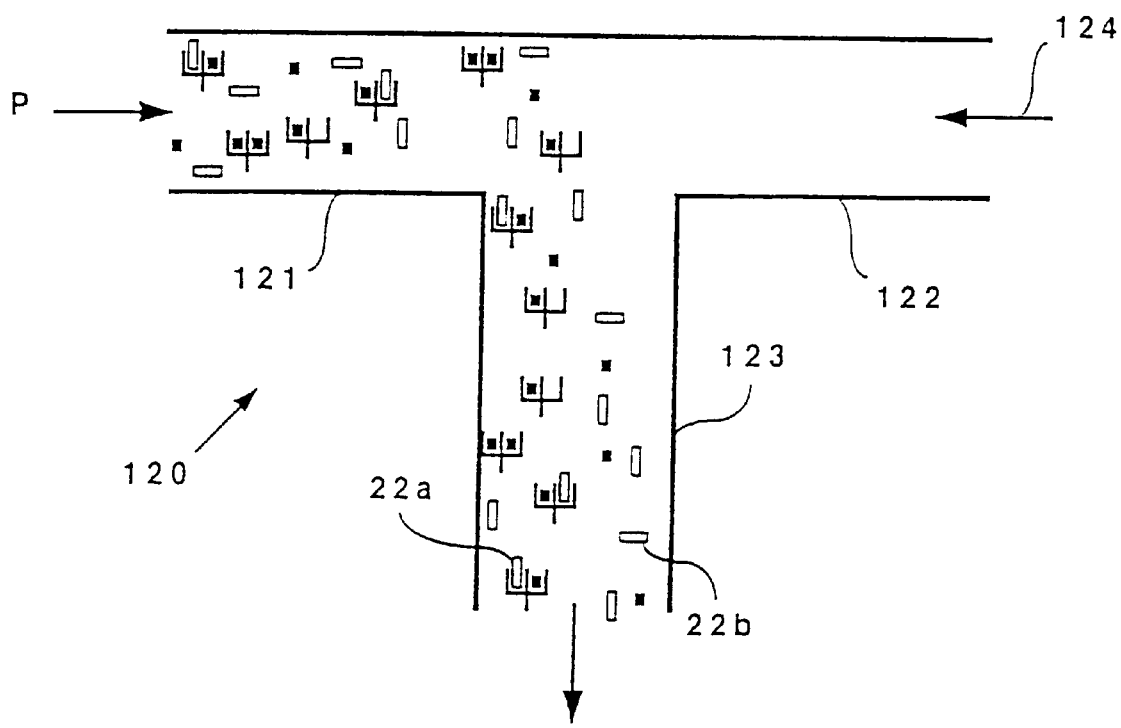
FIG. 7 is a T separator for use with optical detection.

In the embodiment of FIG. 7, the optical measurement is facilitated by diffusional separation of the unbound antigen. The product stream enters detection channel system 120 through product stream channel 121 which, if there are no intervening elements, is product stream channel 50 of the H reactor. Extraction fluid stream 124 enters through extraction stream inlet 122. The extraction fluid can be any fluid capable of accepting particles diffusing from the product stream. Preferred extraction streams comprise water and isotonic solutions such as salt water or organic solvents like acetone, isopropyl alcohol, ethanol, or any other convenient liquid which does not interfere with the product particles or the detection means. The streams join in adjacent laminar flow in joining channel 123. Both separation and detection take place in the joining channel. Free antigen 22b diffuses more rapidly than bound antigen 22a. To select between the bound and unbound antigen, photo illumination or detection is focused on one side of channel 123.

Figure 8:
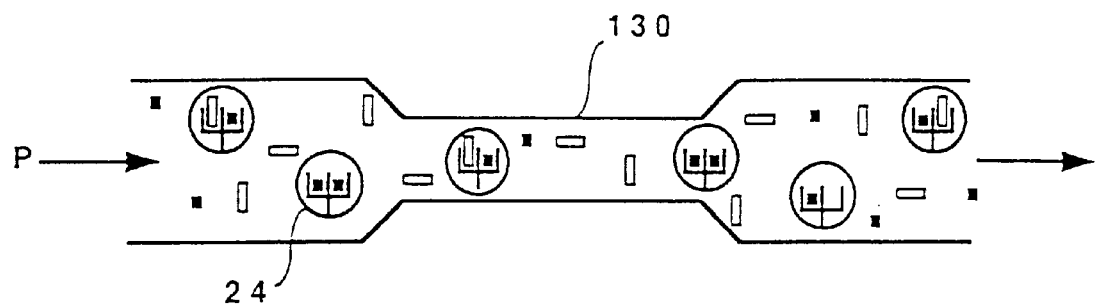
FIG. 8 is a single particle detection channel for use with optical detection.

Another embodiment of optical detection uses single particle detection, for example as in flow cytometer detection channel 130, shown in FIG. 8. The product stream contains particles which are formed into a single file for the flow cytometer. This is particularly suitable for product streams containing reporter beads 24. As illustrated, the smaller particles are not necessarily single file. One embodiment of the flow cytometer uses a v-groove flow channel. The v-groove channel is described in detail in U.S. patent application Ser. No. 08/534,515, filed Sep. 27, 1995, which is incorporated by reference herein in its entirety. The cross-section of such a channel is like a letter V, and thus is referred to as a v-groove channel. The v-groove preferably has a width small enough to force the particles into single file, but large enough to pass the largest particles without clogging. An optical head comprising a laser and small and large angle photodetectors adapted for use with a v-groove flow channel can be employed.

An alternative means of achieving single file particle flow through a flow channel is the sheath flow module disclosed in U.S. patent application Ser. No. 08/823,747, filed Mar. 26, 1997 and incorporated in its entirety by reference herein. The sheath flow module includes sheath fluid inlets before and after, and wider than, a sample inlet. The product stream is surrounded by sheath fluid, and the sheathed stream is focused to produce single file particles.

In dual detection embodiments of the invention, residual sample stream 41 is coupled with a flow cytometer. Alternatively, the fluid stream can flow first through a flow cytometer and then through the H reactor. This allows independent detection of both the smaller and larger analyte particles, for example both undissolved and dissolved analytes or both antigens and cells.

Figure 9:
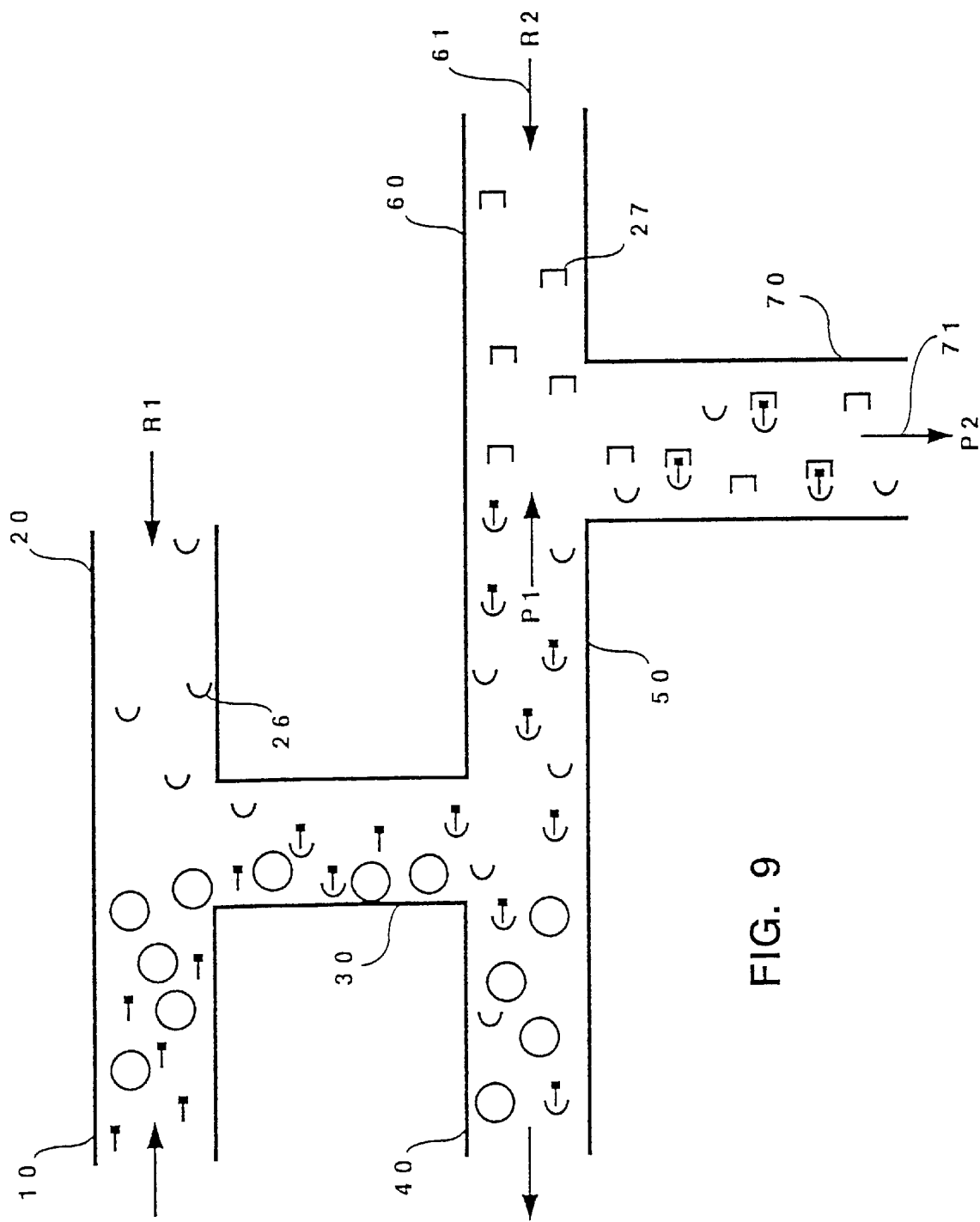
FIG. 9 is an H reactor with a first reagent inlet followed by a T reactor with a second reagent inlet, illustrated with a sandwich inununoassay.

The channel cell of this invention can be used to introduce two reagent streams, a first reagent stream in the H reactor and a second reagent stream in either a T reactor or a second H reactor. For example, in a sandwich immunoassay primary and secondary antibodies can be separately introduced, as shown in FIG. 9. The H reactor comprises sample stream inlet channel 10, first reagent stream inlet channel 20, reaction channel 30, residual sample stream outlet channel 40 and product stream channel 50. The first reagent stream contains primary antibody 26, which reacts with antigen in the sample to form a first product stream, P1.

A second reagent is introduced to the first product in reagent stream 61 (R2) through second reagent stream inlet channel 60. The second reagent stream contains labeled secondary antibodies 27. The first product stream and second reagent stream flow in adjacent laminar streams in joining channel 70, which functions as a reaction channel. In this illustration, the reaction channel is sufficiently long to allow both the first product particles and the second reagent particles to diffuse to the adjacent stream. In one embodiment, the first or second reagent particles are immobilized on magnetic beads and a magnetic field is used to pull the beads to one side of channel 70 for reaction. The beads can remain on that side or be pulled to the other side with a reversed field.

A second product stream, P2, exits in stream 71 through channel 70. Having first and second reagent inlets can be useful, for example, to allow undesirable side reactions to go to completion before the addition of the second reagent. Particles diffuse between the first product and second reagent streams to form a second product. The second product stream 71 the enters a detection channel, for example an optical detection channel as illustrated in FIGS. 5–8.

In generic terms, stream 61 is a companion stream to the first product stream. After diffusion of small particles between the companion stream and the first product stream, which takes place in second laminar flow channel 70, the streams are termed diffused first product and diffused companion streams.

Figure 10:
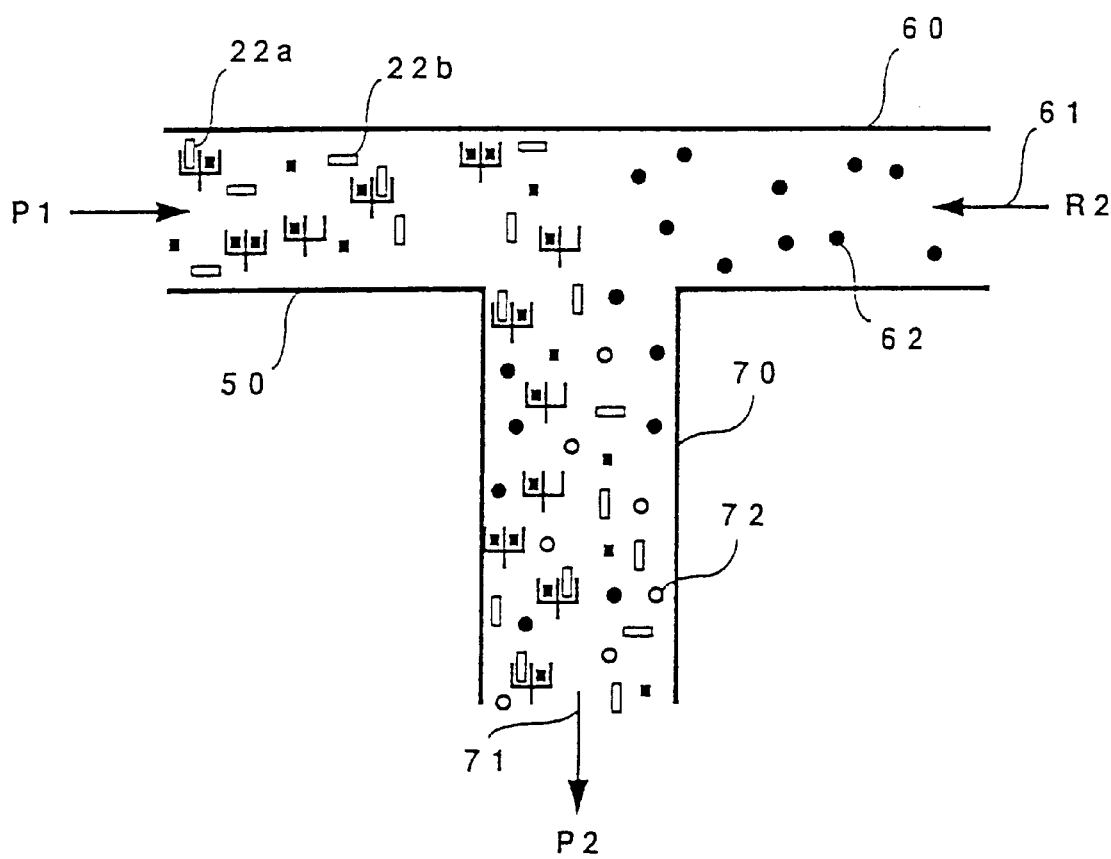
FIG. 10 is a T reactor for use in combination with an H reactor, illustrated with the reaction of an enzymatically labeled antigen.

Another application of a second reagent channel is for chemical detection of product particles. In the above examples, the reagent particles are fluorescently labeled. They can alternatively be chemically labeled, for example enzymatically labeled. In the embodiment of FIG. 10, the antigen in the first reagent is enzymatically labeled. The first product stream flows out of the H reactor (not shown) in product stream channel 50. It contains some bound antigen 22a and some unbound antigen 22b which has been displaced from the antibody by the native antigen from the sample. The enzymatic activity is different in the bound and unbound antigen, typically the unbound antigen is more active. Enzyme substrate particles 62 in second reagent stream 61 enter through second reagent stream inlet channel 60. In joining (reaction) channel 70 they react with the labeled antigen to produce enzyme product particles 72. Second reaction stream 71 flows into a detection channel to detect the enzyme product optically or otherwise. From the amount of enzyme product detected, the amount of antigen in the sample stream can be calculated.

In yet another embodiment, reagent particles 62 react with a first product particle to form a chemiluminescent or bioluminescent product. The luminescence is optically detected. Chemiluminescent reagents are readily available (see, for example, "Tropix Luminescence Products", 1997, Perkin Elmer Applied Biosystems, Bedford, Mass.). Luminescent reagents can also be bound to antibodies and antigens to make luminescently labeled reagent particles.

Figure 11:
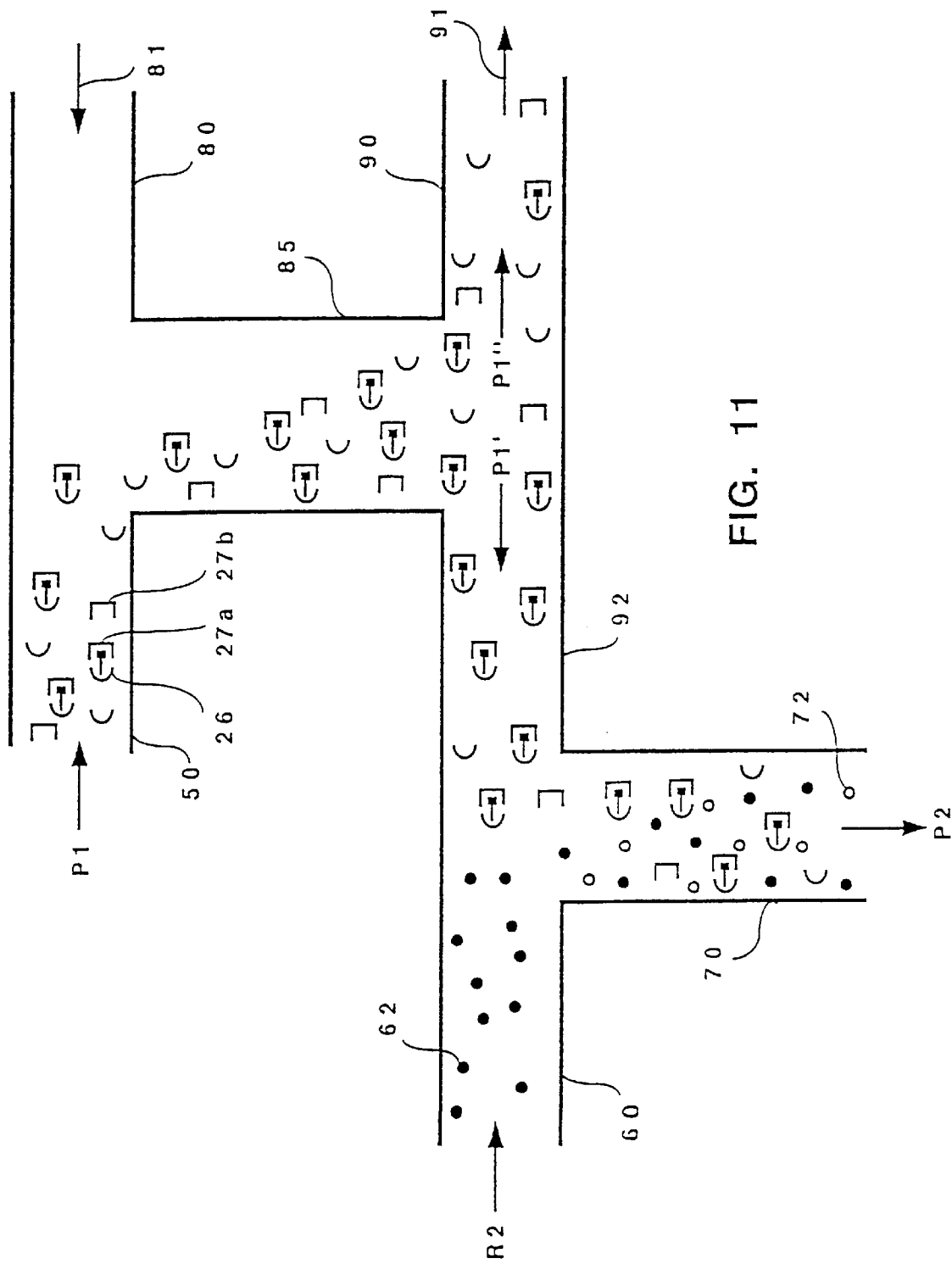
FIG. 11 is an H filter and a T reactor for use in combination with an H reactor, illustrated with a sandwich immunoassay with subsequent selection of the sandwich complex, followed by reaction of an enzymatically labeled antibody with a substrate.
Figure 12:
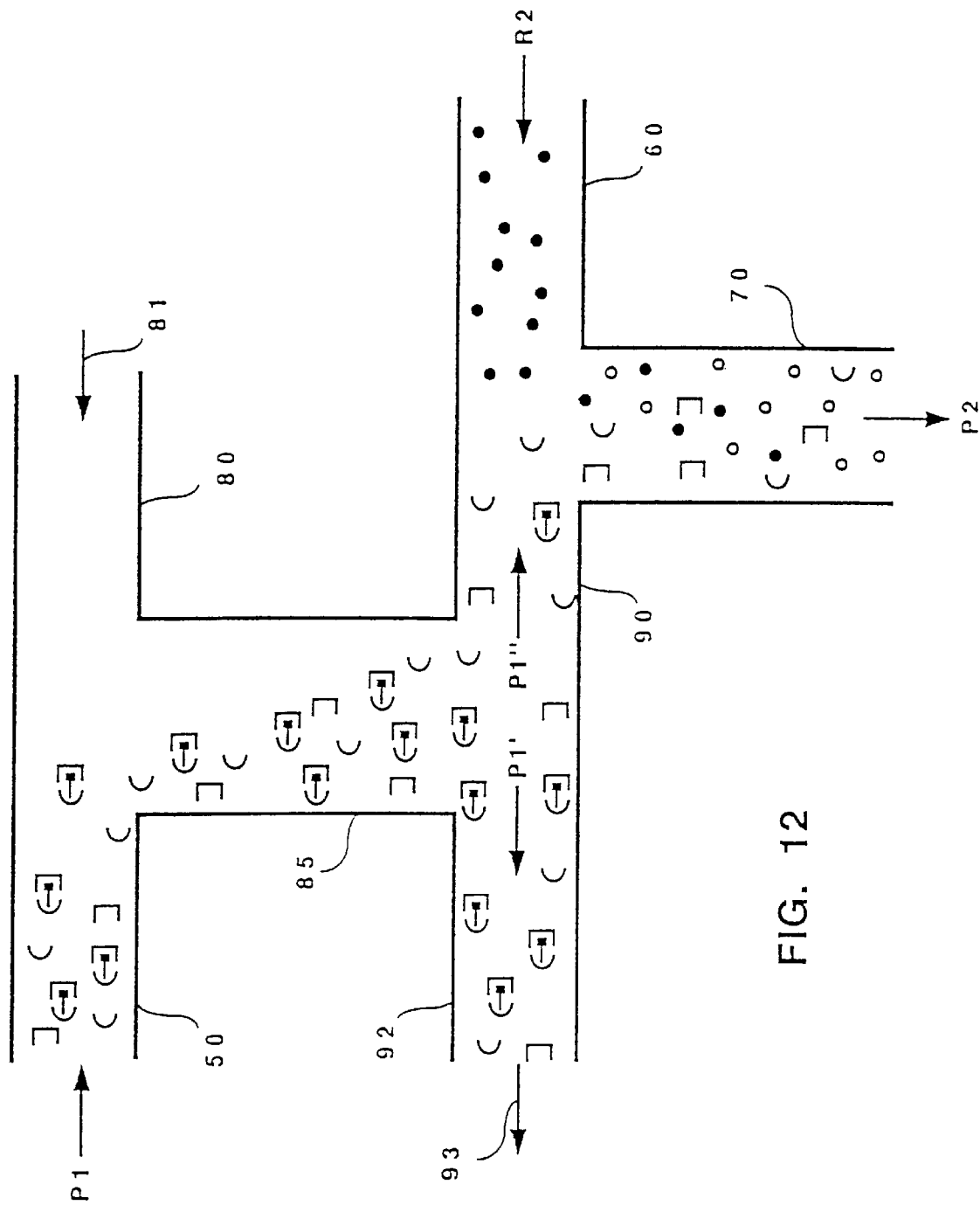
FIG. 12 is an H filter and a T reactor for use in combination with an H reactor, illustrated with a sandwich immunoassay with subsequent selection of the uncomplexed antibody, followed by reaction of an enzymatically labeled antibody with a substrate.

In a sandwich immunoassay the secondary antibody can likewise be enzymatically labeled as shown in FIGS. 11–12. These embodiments further illustrate an H separator between the H reactor and the T reactor. First product stream P1 leaves the H reactor (not shown) through first product stream channel 50. In the illustrated embodiment one type of product particles is a sandwich of native antigen between primary antibody 26 and enzymatically labeled secondary antibody 27a. The sandwich product particles can be formed in a single step, as in FIG. 2, or in two steps, as in FIG. 9. The product stream contains both bound labeled antibodies 27a and unbound labeled antibodies 27b. Rather than distinguish them based on relative chemical activity, they can be separated by diffusion prior to the second reaction.

These embodiments include an H separator. The product stream enters through channel 50 and a companion stream, extraction stream 81, enters through extraction stream inlet 80. The two streams flow in adjacent laminar streams in separation channel 85. The smaller product particles, in this case the unbound antibodies, diffuse into the extraction stream faster than the sandwich complex. The two product streams, the residual first product stream P1' containing the larger particles and the diffused first product stream P1" containing the smaller particles, are separated into channels 92 and 90, respectively.

In the embodiment of FIG. 11 the larger particles enter a T reactor. In reaction channel 70, the product stream flows adjacent to a companion stream, the second reagent stream, which enters through inlet channel 60. Enzyme substrate 62 is converted into enzyme product 72, which flows out in product stream P2 for subsequent detection. In the embodiment of FIG. 12, the lighter product stream in channel 90 meets the second reagent stream, which enters through channel 60, in reaction channel 70. Again the enzyme substrate is converted to enzyme product, which is subsequently detected.

In addition to the product stream outlets illustrated above, additional outlets can be provided for conducting specimen streams from the product stream channel, or at successive intervals along the length of the reaction channel. The specimen channels can be, for example, smaller channels branching from the reaction or product channels. Analyte concentration can be measured in the specimen streams by means such as viewports, fluorescence detectors or flow cytometers.

The length of the reaction channels and the distance traveled by the product stream prior to detection can be selected to allow reactions to go to completion, to limit the sampling of constituents based on their diffusion constants, and to alter the efficiency of separation of particles. The reaction channel is long enough to permit small analyte particles to diffuse from the sample stream and have a detectable effect on reagent particles, preferably at least about 2 mm long. The diffusion time required depends on the diffusion coefficient of the analyte particles. The reaction time required depends on the reaction rate. Some reactions, such as ion reactions, are completed within microseconds. Some reactions, such as competitive immunoassays that involve unloading a bound antigen, require minutes. To allow greater time for reaction between the analyte particles and the reagent particles, the length of the product stream channel can be increased.

The length of the flow channel depends on its geometry. The flow channel can be straight or convoluted. Convoluted channels provide longer distances for diffusion or reaction to occur without increasing the size of the substrate plate in which the channel is formed, thereby allowing for measurement of analytes with smaller diffusion coefficients or reaction rates. The diffusion coefficient of the analyte, which is usually inversely proportional to the size of the analyte, affects the desired reaction channel length. For a given flow speed, particles with smaller diffusion coefficients require a longer flow channel to have time to diffuse into the reagent stream. In preferred embodiments of this invention the channel length of a straight reaction channel is between about 5 mm and about 50 mm. In embodiments of this invention wherein the reaction channel is convoluted, the length of the channel is defined or limited only by the size of the microchip or other material into which the channel is etched or otherwise formed.

As an alternative to increasing channel length to allow more diffusion or reaction of analyte particles, the flow rate can be decreased or the flow may be stopped to allow reactions to proceed and then restarted. However, several factors limit the minimum flow rate. First, the flow rate is typically achieved by a pumping means and some types of pumps cannot produce as low a pressure and flow rate as may be desired to allow enough time for diffusion of the particles. Second, if the flow rate is too slow, particles more dense than the surrounding fluid may sink to the bottom of the flow channel and particles less dense than the surrounding fluid may float to the top of the flow channel. It is preferable that the flow rate be fast enough that hydrodynamic forces substantially prevent particles from sinking to the bottom, floating to the top, or sticking to the walls of the flow channel. In some applications, notably use in space, sedimentation is not a factor. Sedimentation can be avoided by orienting the channel cell with the laminar flow reaction channel vertical.

The flow rate of the input streams is preferably between about 5 micrometers/second and about 5000 micrometers/ second, more preferably about 25 micrometers/second. Preferably the flow rate for both the sample and reagent streams is the same.

By adjusting the configuration of the channels in accordance with the principles discussed above to provide an appropriate channel length, flow velocity and contact time between the sample stream and the reagent stream, the size of the particles remaining in the sample stream and the particles diffusing into the reagent stream can be controlled. The contact time required can be calculated as a function of the diffusion coefficient of the particle and the distance over which the particle must diffuse. If the diffusion coefficient of the larger particles is about ten times smaller than the coefficient for the analytes, the product stream should be substantially free of the large particles.

Figure 13:
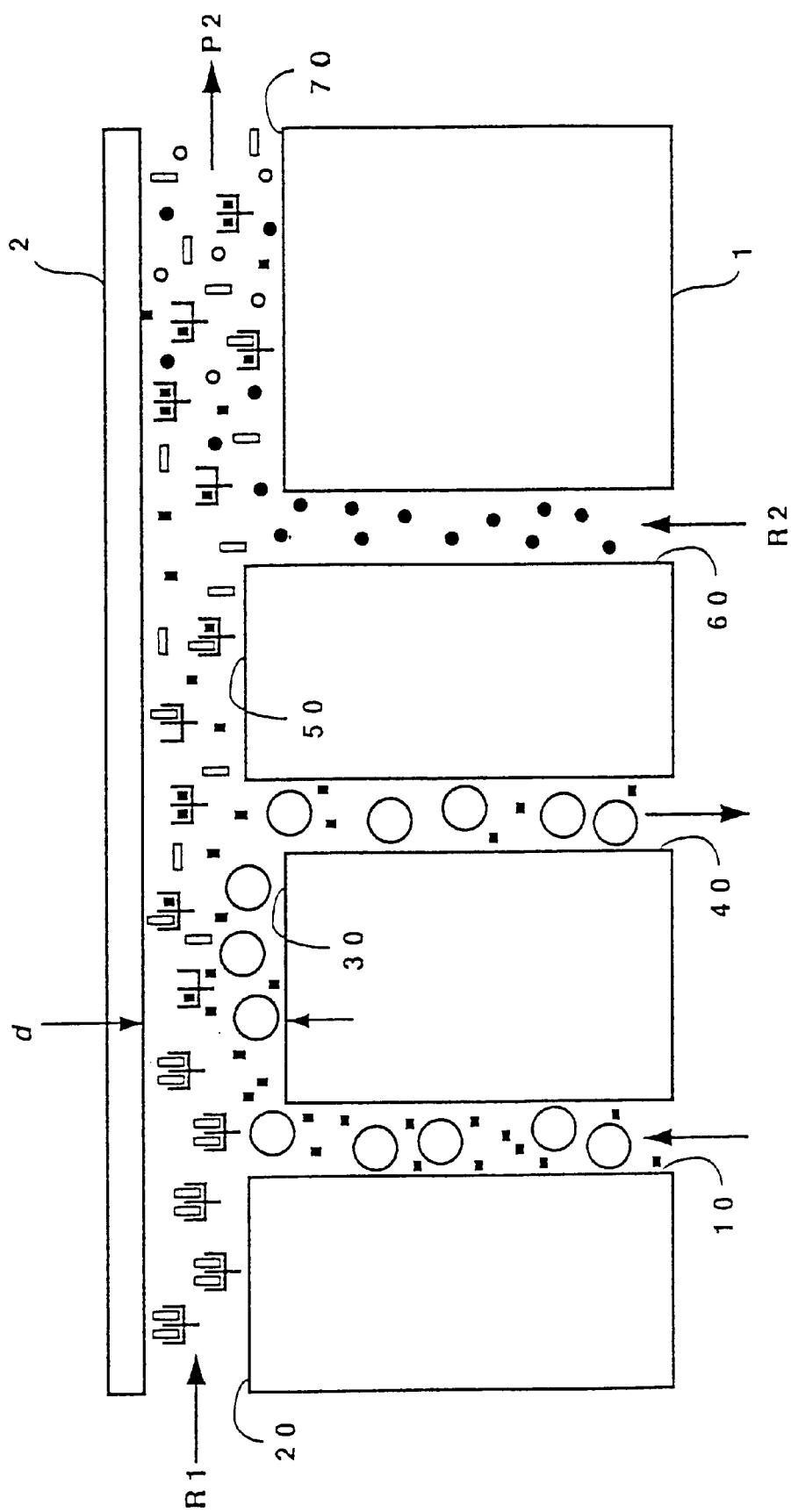
FIG. 13 is an H reactor and subsequent T reactor with diffusion in the plane perpendicular to the channel cell surface, illustrated with a competitive immunoassay and subsequent reaction of an enzymatically labeled antigen with a substrate.

The channel cell of this invention has been demonstrated with diffusional separation occurring in a plane parallel to the channel cell surface, termed the parallel embodiment. The channels can alternatively be formed so that the diffusional separation takes place in a plane orthogonal to the channel cell surface. FIG. 13 is a cross section of an H reactor and a T reactor formed in the orthogonal plane, termed the orthogonal embodiment. The channels are formed between substrate plate 1 and coverplate 2. The H reactor is formed by sample (primary) stream inlet channel 10, first reagent stream inlet channel 20, reaction channel 30, residual sample stream outlet channel 40 and first product stream channel 50. The first reagent stream inlet can, like the sample inlet, feed through the substrate plate.

As in the parallel configuration, the diffusion direction is termed the depth, labeled d, but note that the diffusion direction, and hence the depth, in FIG. 13 is orthogonal to the diffusion direction in FIG. 1. The depth of channel 30 is optionally greater than the depth of channels 20 and 50 to accommodate two streams. Although this H reactor does not have the visual appearance of the letter "H", it has the functional criteria of two laminar flow channels joining in the upstream end of a reaction channel to form adjacent flow streams, layered in this case rather than side by side, and two laminar flow channels branching from the downstream end of the reaction channel.

The product stream of the H reactor of FIG. 13 enters a T reactor comprising product stream channel 50, second reagent stream inlet channel 60, and reaction channel 70. The depth of channel 70 is optionally greater than the depth of channel 50 to accommodate two streams. In the previous embodiments (see FIG. 9, for example), channels 50 and 60 were collinear, in this embodiment they join at a right angle. As in the case of the H reactor, it is not the visual appearance of the letter "T" that defines the T reactor, but rather the functional criteria of the product stream channel joining a companion stream inlet channel to form adjacent laminar streams in the reaction channel.

The perpendicular embodiment can have a larger contact area between the sample and reagent streams than the parallel version. The width of the flow channel in the perpendicular embodiment can be increased to increase the contact area while maintaining laminar flow. This allows a greater reaction volume, which is particularly advantageous for the synthesis application of the device. The parallel embodiment is cheaper and easier to fabricate, which is particularly advantageous in the analysis application of the device.

In either the parallel or perpendicular embodiment, the channel cell is generally formed by two plates with abutting surfaces. The channels may be formed in both plates, or one plate can contain the channels and the other can be a flat cover plate. The channel cells of this invention may be formed by any techniques known to the art. Silicon channel plates are preferably formed by etching the flow channels onto the horizontal surface of a silicon microchip and placing a cover plate, preferably of an optically clear material such as glass or a silicone rubber sheet, on the etched substrate plate. To promote flow, the corners can be etched. For non-silicon channel plates, other means for manufacturing the channel cells of this invention include molding the device in plastic, micromachining, and other techniques known to the art. Precision injection molded plastics can also be used to form the devices. In a preferred embodiment of this invention, channel cells have hydrophilic surfaces to facilitate flow of liquid therein and allow operation of the device without the necessity for pressurization. The substrate may be treated by means known to the art following fabrication of the channels to render it hydrophilic. The cover plate is also preferably treated to render it hydrophilic.

For optical detection in transmission, such as absorbance detection, the analyte detection area, and optionally other parts of the channel cell system, are optically accessible. Typically the detection area lies between optically transparent plates. Analyte detection area as used herein refers to that portion of a flow channel where changes in the analyte particles or the reagent particles are measured. For detection with reflection, such as fluorescence or luminescence detection, only one plate need be transparent, typically the cover plate. For product synthesis, the channel system need not be transparent in any portion.

The preferred channel dimensions depend on the application, with the criterion that laminar flow must be maintained. The channel depth (diffusion direction) is preferably between about 10 and 1000 $\mu$m, and most preferably around 400 $\mu$m, in both the parallel and perpendicular embodiments. The channel width is about 10–200 $\mu$m in the parallel embodiment. In the perpendicular embodiment, it can be more than several millimeters wide and still maintain laminar flow.

Means for applying pressure to the flow of the feed fluids through the device can also be provided. Such means can be provided at the inlets and/or the outlets (e.g. as vacuum exerted by chemical or mechanical means). Means for applying such pressure are known to the art, and include the use of a column of water or other means of applying water pressure, electroendoosmotic forces, optical forces, gravitational forces, and surface tension forces. The outlets can be connected to fluid receptacles. Such receptacles may be coupled to an analytical or detection device.

Figure 14:
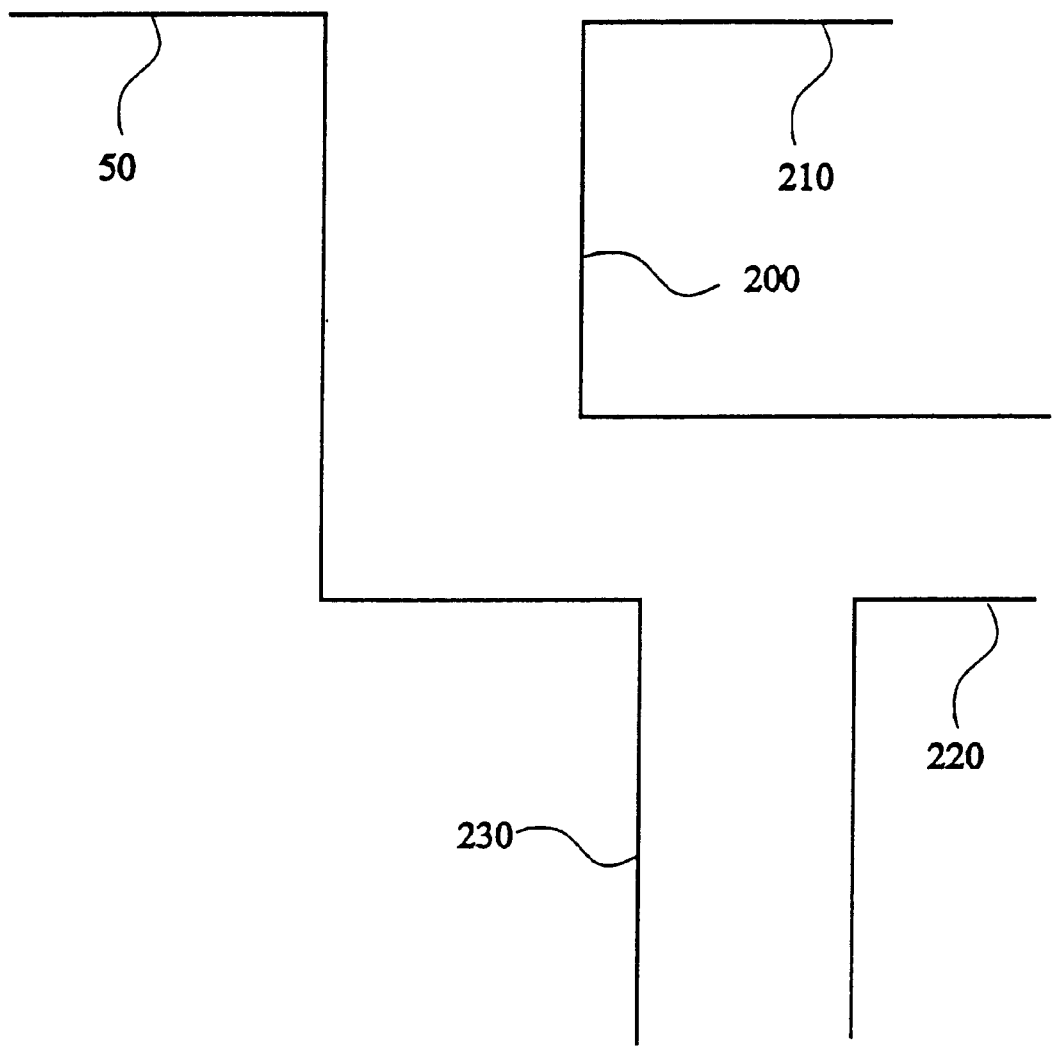
FIG. 14 shows an embodiment in which an H-filter (not shown) is connected to two T-reactors in series.

FIG. 14 shows an embodiment in which the product stream channel 50 of an H-filter (not shown) is connected to the upstream end of a second laminar flow channel 200 at the opposite side of which is provided a second companion reagent stream inlet channel 210. The downstream end of second laminar flow channel 200 is connected to the upstream end of third laminar flow channel 230. Connected to the upstream end of third laminar flow channel 230 is third companion reagent stream inlet 220.

Various aspects of this invention have been illustrated with specific examples. Combinations and variations of these embodiments will be readily apparent to those skilled in the art and fall within the spirit and scope of this invention. For example, any of the exemplified configurations and reaction schemes can be implemented with reagent particles immobilized on beads. The beads can be magnetic and magnetic fields can be used to manipulate the beads.

Filters, diffusion based or otherwise, can be placed before or after the H reactor, and can be positioned between the H reactor and subsequent reactors, separators and detectors. Each reagent stream can contain more than one type of reagent particle for detection of a single type of analyte particle or for simultaneous detection of multiple analytes. More than one reagent stream channel can join the upstream end of the reaction channel, or more than one reagent stream channel can merge prior to joining the reaction channel. More than one product stream channel can leave the downstream end of the reaction channel. In addition to detecting species in the product stream, the residual sample stream and any of the companion streams can be analyzed. The angles of the "H" and "T" are not limited to right angles. Parallel and perpendicular geometries can be combined in one channel system. This reactor can be used in combination with other sample preparation and analysis apparatus.

EXAMPLE 1

Tests performed by EMIT (Enzyme Multiplied Immunoassay Technique) can be carried out in the H reactor combined with the T reactor of this invention. EMIT is a homogeneous immunoassay for low-molecular-weight ligands. The assay is based on binding of antibody to an enzyme labeled ligand in order to change the enzyme activity. The competitive binding of antibody bound and unbound ligands is used to measure the concentration of unbound ligand. Here, digoxin, a drug used to control cardiac arrhythmias and requiring frequent concentration analysis in case of intoxication, is selected as an example test. The EMIT assay for digoxin is based on the competitive binding between drug in the sample and drug labeled with glucose-6-phosphate dehydrogenase made using recombinant DNA technology (rG6P-DH) for antibody binding sites. The drug concentration is measured through enzyme activity which decreases upon binding to the antibody. Active enzyme reduces NAD to NADH.

The reaction is illustrated in FIG. 1 combined with FIG. 10. In this assay, reagent stream R1 contains digoxin labeled with glucose-6-phosphate dehydrogenase 22 and antibody 23. Reagent stream R1 is imported through channel 20 and contacts the sample stream from channel 10. Digoxin in the sample 12 diffuses into the reagent stream in channel 30, binds with antibody and is transported to channel 50, while cellular components are transported to channel 40. The more digoxin molecules in the sample stream, the more antibody binds with free digoxin instead of enzyme labeled digoxin. As a result, the more enzyme is freed from antibody binding.

In channel 70, the product stream encounters reagent stream R2, containing two types of reagent particles, the substrate glucose-6-phosphate (not shown) and NAD 62. Freed enzyme oxidizes glucose-6-phosphate and reduces NAD to NADH 72. In the second product stream, the residual enzyme activity is measured by spectroscopy through the change in absorbance by NADH at 340 nm.

EXAMPLE 2

In another embodiment using multiple reagents in series, the sample stream is blood to be analyzed for glucose, the first reagent stream R1 contains glucose oxidase, and the second reagent stream R2 contains a pH sensitive dye. In channel 30 glucose particles from the blood diffuse into the reagent stream and are changed to gluconic acid. In channel 70 the gluconic acid reacts with the pH-sensitive dye. In the second product stream, the reaction is detected by changes in the dye absorbance.

We claim:
1. A microchannel system comprising:
   a first laminar flow channel having an upstream end and a downstream end and having first and second sides;
   a primary stream inlet channel, containing a flowing primary stream, connected to said first side of said upstream end of said first laminar flow channel;
   a first companion stream inlet channel, containing a flowing first companion stream, connected to said second side of said upstream end of said first laminar flow channel;
   a residual primary stream outlet channel, containing a flowing residual primary stream, connected to said first side of said downstream end of said first laminar flow channel;
   a first product stream channel, containing a flowing first product stream having an upstream end and a downstream end, said upstream end of said product stream channel connected to said second side of said downstream end of said first laminar flow channel;
   a second laminar flow channel having an upstream end and a downstream end, and connected at said upstream end to said downstream end of said first product stream channel; and
   a second companion stream inlet channel, containing a flowing second companion stream, connected to said upstream end of said second laminar flow channel, whereby said first product stream, and said second companion stream flowing into said second laminar flow channel through said second companion stream inlet channel, flow in adjacent laminar streams in said second laminar flow channel.

2. The microchannel system of claim 1 wherein said first product stream channel is convoluted.

3. The microchannel system of claim 1 wherein said second companion stream is an extraction stream.

4. The microchannel system of claim 1 wherein said primary stream inlet channel contains a flowing stream of whole blood comprising first antigens.

5. The microchannel system of claim 4 wherein said first companion stream inlet channel contains a flowing first companion stream comprising antibodies bound to labeled antigens identical to said first antigens.

6. The microchannel system of claim 5 wherein said second laminar flow channel contains a flowing stream comprising unbound labeled antigens identical to said first antigens.

7. The microchannel system of claim 6 comprising means for detecting said unbound labeled antigens.

8. The microchannel system of claim 6 wherein said second companion stream inlet channel contains a flowing extraction stream.

9. The microchannel system of claim 4 wherein said first companion stream inlet contains a flowing first companion stream comprising labeled antigens identical to said first antigens attached to beads.

10. The microchannel system of claim 1 wherein:
   said primary stream inlet channel contains a flowing stream of whole blood comprising first antigens;
   said first companion stream inlet channel contains a flowing first companion stream comprising second antigens identical to said first antigens bound to an enzyme and to antibodies capable of binding to said first and second antigens;
   said second companion stream inlet channel contains a flowing second companion stream comprising substrate for said enzyme; and said second laminar flow channel contains a flowing stream comprising enzyme product formed by reaction of said substrate with said enzyme.

11. The microchannel system of claim 1 wherein:

said primary stream inlet channel contains a flowing stream of whole blood comprising first antigens;

said first companion stream contains primary antibodies capable of binding to said first antigens; and said second companion stream comprises labeled secondary antibodies capable of binding to said antigens.

12. The microchannel system of claim 11 wherein said second laminar flow channel comprises a flow cytometer at said downstream end.

13. The microchannel system of claim 11 wherein said primary antibodies are attached to beads.

14. The microchannel system of claim 11 comprising detection means for detecting a labeled secondary antibody attached to said beads.

15. The microchannel system of claim 1 wherein:

said primary stream inlet channel contains a flowing stream of whole blood comprising first antigens;

said first companion stream contains primary antibodies capable of binding to said antigens and labeled secondary antibodies capable of binding to said antigens; and said second companion stream is an extraction stream.

16. The microchannel system of claim 1 wherein:

said primary stream contains a flowing stream of whole blood comprising substrate particles;

said first companion stream is an extraction stream;

said first product stream contains said substrate particles;

said second companion stream contains enzyme for said substrate particles; and said second laminar flow channel contains product particles produced by reaction between said substrate and enzyme particles.

17. The microchannel system of claim 16 comprising:

a third laminar flow channel having an upstream end and a downstream end, said upstream end connected to the downstream end of said second laminar flow channel; and a third companion stream inlet containing a flowing third companion stream connected to the upstream end of said third laminar flow channel comprising indicator particles capable of making a detectable change when contacted by said product particles.

18. The microchannel system of claim 1 wherein:

said primary stream inlet channel contains a flowing stream of whole blood comprising virus; and said first companion stream contains antibodies to said virus attached to magnetic beads;

said microchannel system also comprising:

a flow cytometer connected to said downstream end of said second laminar flow channel;

means for exerting a magnetic field to push said magnetic beads to said first side of said first laminar flow channel; and means for exerting a magnetic field to push said magnetic field to said second side of said first laminar flow channel;

wherein:

said first product stream channel comprises viruses bound to said antibodies attached to said magnetic beads;

said first companion stream contains labeled secondary antibodies to said virus; and said second laminar flow channel comprises said secondary antibodies bound to said beads.

19. The microchannel system of claim 1 further comprising a detection channel connected to said downstream end of said second laminar flow channel.

20. The microchannel system of claim 19 wherein said detection channel is optically accessible.

21. The microchannel system of claim 19 wherein said detection channel is convoluted.

22. The microchannel system of claim 19 wherein said detection channel comprises a flow cytometer channel.

23. The microchannel system of claim 22 wherein said flow cytometer channel comprises a sheath flow module.

24. The microchannel system of claim 22 wherein said flow cytometer channel is a v-groove.

25. The microchannel system of claim 1 further comprising:

a first outlet stream channel having an upstream end and a downstream end, said upstream end connected to said downstream end of said second laminar flow channel.

26. The microchannel system of claim 25 further comprising a detection channel connected to said downstream end of said first outlet stream channel, said detection channel comprising detection means.

27. The microchannel system of claim 26 further comprising a third laminar flow channel connected to the downstream end of said second laminar flow channel, said third laminar flow channel having an upstream end and a downstream end.

28. The microchannel system of claim 27 further comprising a third companion stream inlet channel containing a flowing third companion stream connected to the upstream end of said third laminar flow channel.

29. The microchannel system of claim 28 wherein:

said primary stream inlet channel contains a flowing stream of whole blood comprising first antigens;

said first companion stream comprises primary antibodies capable of binding to said first antigens;

said second companion stream comprises labeled secondary antibodies capable of binding to said first antigens; and said third companion stream is an extraction stream.

30. The microchannel system of claim 28 further comprising a second outlet stream channel connected to said downstream end of said second laminar flow channel.

31. The microchannel system of claim 30 further comprising:

a third laminar flow channel having an upstream end and a downstream end, said upstream end connected to said downstream end of said first outlet stream channel; and a third companion stream inlet channel containing a third companion inlet stream connected to said upstream end of said third laminar flow channel.

32. The microchannel system of claim 31 also comprising:

means for exerting a magnetic gradient to push said magnetic beads to a first side of said second laminar flow channel, said first side of said second laminar flow channel being connected to said first outlet channel; wherein said primary stream inlet channel contains a flowing stream of whole blood comprising first antigens;

said first companion stream inlet channel contains a first companion stream comprising primary antibodies capable of binding to said first antigens bound to magnetic beads;

said second companion stream inlet channel contains a second companion stream comprising secondary antibodies capable of binding to said first antigens linked to enzymes in buffer;

said first outlet channel contains a flowing stream comprising said magnetic beads, antibodies and enzyme;

said second outlet channel contains a flowing stream comprising buffer; and said third laminar flow channel contains a flowing stream comprising product particles produced by reaction of said enzyme and said substrate.

33. The microchannel system of claim 32 wherein said third laminar flow channel is convoluted.

34. The microchannel system of claim 32 also comprising detection means for detecting said product particles in said third laminar flow channel.

35. The microchannel system of claim 31 wherein:

said primary stream inlet channel contains a flowing stream of whole blood comprising first antigens;

said first companion stream inlet channel contains a first companion stream comprising primary antibodies capable of binding to said first antigens and secondary antibodies capable of binding to said first antigens bound to enzyme;

said second companion stream inlet channel contains a flowing extraction stream;

said third companion stream comprises substrate for said enzyme;

said first outlet channel contains a flowing stream comprising complexes of said antigens, said secondary antibodies, said enzyme, and said primary antibodies;

said second outlet channel contains a flowing stream comprising secondary antibodies bound to enzyme; and said third laminar flow channel contains a flowing stream comprising product particles produced by reaction of said enzyme and said substrate.

36. The microchannel system of claim 35 wherein said third laminar flow channel is convoluted.

37. The microchannel system of claim 35 also comprising detection means for detecting said product particles in said third laminar flow channel.

38. The microchannel system of claim 1 further comprising:

a third companion stream inlet connected to said second laminar flow channel downstream from said second companion stream inlet.

39. The microchannel system of claim 1 further comprising a third companion stream inlet channel containing a flowing third companion stream connected to said first laminar flow channel downstream from said first companion stream inlet and upstream from said second companion stream inlet.

40. The microchannel system of claim 1 further comprising a second product stream outlet channel containing a second product stream connected to said downstream end of said first laminar flow channel.

41. The microchannel system of claim 40 wherein said primary stream inlet channel contains a flowing stream of whole blood comprising first antigens;

said first companion stream inlet channel contains a first companion stream comprising antigens, identical to said first antigens and attached to enzyme, bound to antibodies capable of binding to said antigens, all attached to beads;

said second companion stream inlet channel contains an extraction stream;

said third companion stream inlet channel contains a third companion stream comprising substrate for said enzyme; and said third laminar flow channel contains a flowing stream comprising enzyme product formed by reaction of said enzyme with said substrate.

42. The microchannel system of claim 1 wherein said system is formed with a substrate plate having channels formed therein and a cover plate bonded to said substrate plate.

43. The microchannel system of claim 42 wherein the configuration of said primary stream inlet and first companion stream inlet is such that said primary and first companion streams flow in side by side laminar streams in said first laminar flow channel.

44. The microchannel system of claim 42 wherein the configuration of said primary stream inlet and first companion stream inlet is such that said primary and first companion streams flow in layered laminar streams in said first laminar flow channel.

45. A microchannel system comprising:

a laminar flow channel having an upstream end and a downstream end, a first side and a second side;

a first inlet channel, connected to the first side of the upstream end of said laminar flow channel, containing a flowing stream of whole blood comprising substrate particles;

a second inlet channel, connected to the second side of the upstream end of said laminar flow channel, containing a flowing stream comprising an indicator material;

a third inlet channel connected to the upstream end of said laminar flow channel between said first inlet channel and said second inlet channel, containing a flowing stream comprising enzyme particles capable of reacting with said substrate particles to form product particles; said product particles being capable of reacting with said indicator material to produce a detectable change; and means for detecting said change.

46. A microchannel system comprising:

a first convoluted laminar flow channel having an upstream end and a downstream end and having first and second sides;

a primary stream inlet channel connected to said first side of said upstream end of said first laminar flow channel;

a first companion stream inlet channel connected to said second side of said upstream end of said first laminar flow channel;

a flow cytometer in said downstream end of said first laminar flow channel;

said primary stream inlet channel containing a flowing stream of whole blood containing antigens; and said first companion stream inlet channel containing a flowing first companion stream comprising labeled antigens identical to said first antigens attached to beads.

47. The microchannel system of claim 46 wherein said first laminar flow channel is convoluted.

48. A microchannel system comprising:

a first convoluted laminar flow channel having an upstream end and a downstream end and having first and second sides;

a primary stream inlet channel connected to said first side of said upstream end of said first laminar flow channel;

a first companion stream inlet channel connected to said second side of said upstream end of said first laminar flow channel;

said primary stream inlet channel containing a flowing stream of whole blood containing antigens;

said first companion stream inlet channel containing a flowing first companion stream comprising labeled antigens identical to said first antigens attached to beads;

a residual primary stream outlet channel connected to said first side of said downstream end of said first laminar flow channel, said residual primary stream outlet containing a residual primary stream comprising whole blood components; and a first product stream channel, having an upstream end and a downstream end, said upstream end of said product stream channel connected to said second side of said downstream end of said first laminar flow channel, said first product stream channel containing a product stream comprising beads attached to labeled antigens identical to said first antigens.

49. The microchannel system of claim 48 also comprising a flow cytometer at the downstream end of said first product stream channel.

50. A microchannel system comprising:

a first laminar flow channel having an upstream end and a downstream end and having first and second sides;

a primary stream inlet channel connected to said first side of said upstream end of said first laminar flow channel;

a first companion stream inlet channel connected to said second side of said upstream end of said first laminar flow channel;

a flow cytometer in said downstream end of said first laminar flow channel;

said primary stream inlet channel containing a flowing stream of whole blood; and said first companion stream inlet channel containing a first companion stream comprising first labeled antibodies capable of binding to red cells and second, differently labeled antibodies capable of binding to white cells.

51. A microchannel system comprising:

a laminar flow channel having an upstream end and a downstream end and having first and second sides;

a primary stream inlet channel, containing a flowing primary stream, connected to said first side of said upstream end of said laminar flow channel;

a first companion stream inlet channel, containing a flowing first companion stream, connected to said second side of said upstream end of said first laminar flow channel, whereby said primary stream and said first companion stream flow in adjacent laminar streams;

a second companion stream inlet channel, containing a flowing second companion stream, connected to said laminar flow channel downstream from said inlet channels; and flow control means in fluid communication with said second companion stream inlet channel, whereby said second companion stream flows into said laminar flow channel.

* * * * *